US00PP09329P

United States Patent [19]

Zary

[11] Patent Number: Plant 9,329

[45] Date of Patent: Oct. 17, 1995

[54] HYBRID TEA ROSE PLANT NAMED 'JACYEM'

[75] Inventor: Keith W. Zary, Thousand Oaks, Calif.

[73] Assignee: Bear Creek Gardens, Inc., Medford, Oreg.

[21] Appl. No.: 366,243

[22] Filed: Dec. 28, 1994

[51] Int. Cl.[6] ..... A01H 5/00

[52] U.S. Cl. ..... Plt./15

[58] Field of Search ..... Plt./15

*Primary Examiner*—Howard J. Locker

*Attorney, Agent, or Firm*—Klarquist Sparkman Campbell Leigh & Whinston

[57] ABSTRACT

A hybrid tea rose plant characterized particularly as to novelty by the unique combination of its large, light yellow flowers; its vigorous, upright habit of growth; its good production of long, straight stems; its strong fragrance; and its dark green, powdery mildew resistant foliage.

1 Drawing Sheet

The present invention relates to a new and distinct variety of rose plant of the hybrid tea class which was originated by me by crossing the variety JACblem, U.S. Plant Pat. No. 4,847 with the variety JACliow, unpatented.

The primary objective of this breeding was to produce a new rose variety having the dark green glossy foliage and powdery mildew resistance, the high production and yellow color of the female parent combined with the good production and large flower size of the male parent. The objective was substantially achieved, along with other desirable improvements, as evidenced by the following unique combination of characteristics that are outstanding in the new variety and that distinguish it from its parents, as well as from all other varieties of which I am aware:

1. Large, light yellow flowers.
2. Strong, musky fragrance.
3. Vigorous, upright habit of growth.
4. Good production of long, strong stems.
5. Dark green, glossy, mildew resistant foliage.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—JACblem, U.S. Plant Pat. No. 4847.

*Pollen parent.*—JACliow, unpatented.

Classification:

*Botanical.*—*Rosa hybrida.*

*Commercial.*—Hybrid tea.

FLOWER

Observations made from specimens grown in a greenhouse environment at Somis, Calif. in January through June, 1994.

Blooming habit: Continuous.

Bud:

*Size.*—2 inches long when the petals start to unfurl.

*Form.*—The bud form is long, pointed ovoid.

*Color.*—When sepals first divide, bud color is Yellow Group 8B. When half blown, the upper sides of the petals are Yellow Group 8C; and the lower sides of the petals are Yellow Group 8C.

*Sepals.*—Color: Green Group 138B. Surface texture: Covered in fine hairs. There are three normally to heavily appendaged sepals. There are two unappendaged sepals with hairy edges.

*Receptacle.*—Color: Green Group 137C. Shape: Funnel. Size: ⅜ inch×¼ inch. Surface: Smooth.

*Peduncle.*—Length: 4 inches to 4½ inches. Surface: Smooth. Color. Medium green. Strength: Stiff, erect, heavy.

Bloom:

*Size.*—Large. Average open size is 5 inches to 5½ inches.

*Borne.*—Singly.

*Stems.*—Long, strong. Average length is about 22 inches to 30 inches.

*Form.*—When first open: High centered. Permanence: Retains its form to the end, outer petals curl back.

*Petalage.*—Number of petals under normal conditions: 35 to 40.

*Color.*—The upper side of the petals is Yellow Group 8C. The reverse side of the petals is Yellow Group 8C. The color of the base of each petal is deep Yellow (Yellow Group 13B) at the point of attachment. The major color on the upper side is Yellow Group 8C.

*Variegations.*—Occasional greenish streak on the guard petals.

*Discoloration.*—The general tonality at the end of the first day: No change. At the end of the third day: Little change. In bright sunlight, in a greenhouse, the flower opens and holds the Yellow Group 8C color.

*Fragrance.*—Strong.

Petals:

*Texture.*—Thick.

*Shape.*—Round to slightly deltoid.

*Form.*—Tips slightly recurved, edges slightly quilled.

*Arrangement.*—Imbricated, with few petaloids in the center.

*Persistence.*—Drop off cleanly.

*Lastingness.*—On the plant: Long. As a cut flower: 8 to 9 days.

Reproductive parts:

*Anthers.*—Size: Medium. Quantity: Many. Color: Yellow. Arrangement: Regular around styles.

*Filaments.*—Color: Yellow except at their base where they become red.

*Pollen.*—Color: Gold yellow.

*Styles.*—Color: Red.

*Stigmas.*—Color: Greenish white.

Form: Bush.

Growth: Very vigorous; upright; branching. At one year of age, under normal greenhouse conditions, the producing plant is 6 to 7 feet tall and 4 feet wide, producing 150 stems per square meter of greenhouse.

Foliage: Number of leaflets on normal mid-stem leaves: 5.

*Size.*—Long to very long (8 inches long× 6 inches wide).

*Quantity.*—Abundant.

*Color.*—New foliage: Greyed-Purple Group 183C. Old foliage: Upper side: Green Group 136A; Lower side: Green Group 139C.

Leaflets:

*Shape.*—Pointed oval.

*Texture.*—Upper side: Leathery, glossy.

*Edge.*—Serrated.

*Serration.*—Single, small.

*Petiole rachis.*—Color: Green.

*Petiole underside.*—Smooth.

*Stipules.*—¾ inch long, serrated and glandular.

*Disease resistance.*—Resistant to powdery mildew under normal growing conditions in a greenhouse in Somis, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Medium to short (¼ inch long), hooked downward.

*Color when young.*—Red.

Small prickles:

*Quantity.*—On main stalks: None. On laterals: None.

I claim:

1. A new and distinct variety of rose plant of the hybrid tea class, substantially as herein shown and described, characterized particularly as to novelty by the unique combination of its large, light yellow flowers; its vigorous, upright habit of growth; its good production of long, straight stems; its strong fragrance; and its dark green, powdery mildew resistant foliage.

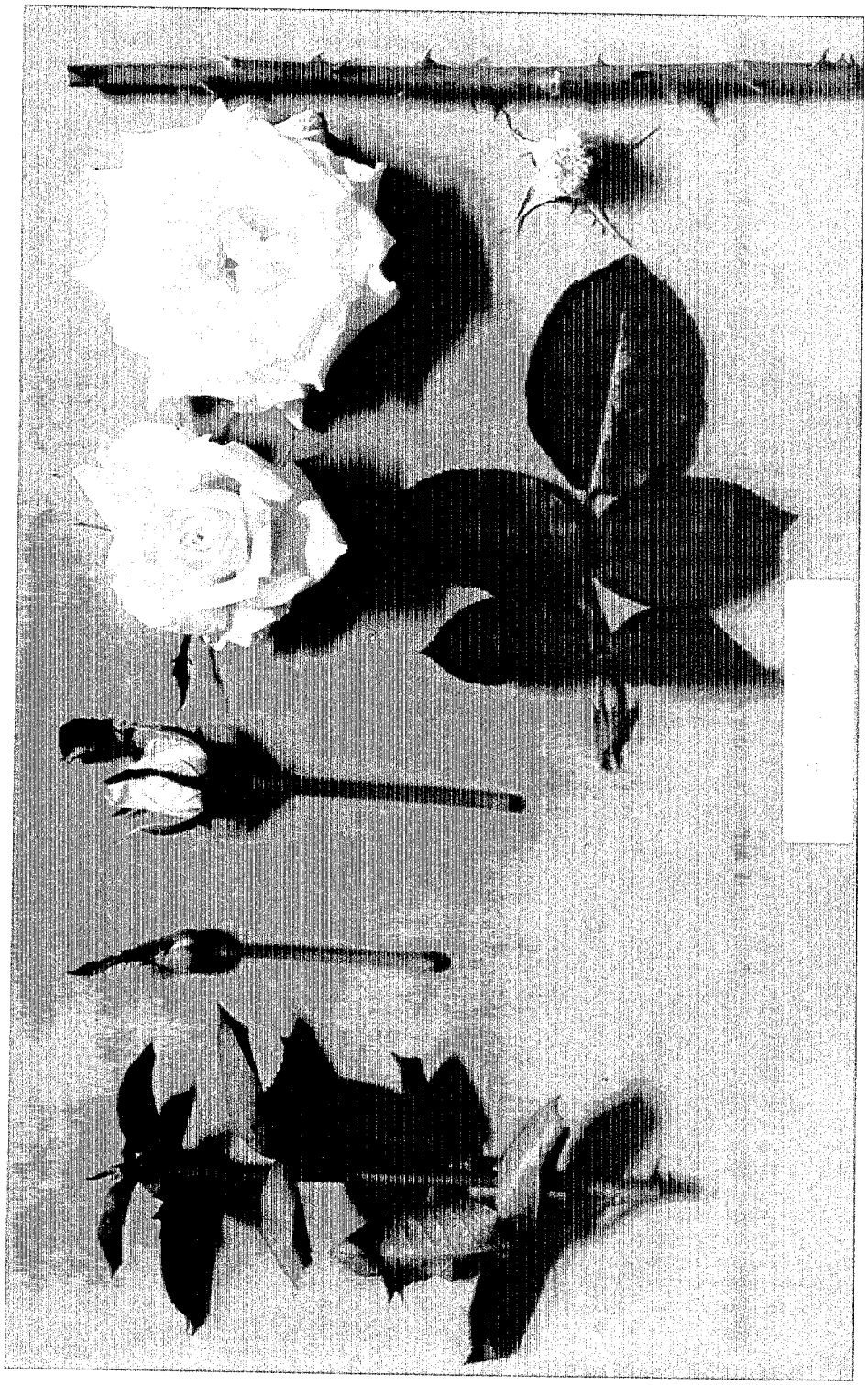

* * * * *